United States Patent
Yamamoto et al.

(10) Patent No.: US 11,897,537 B2
(45) Date of Patent: Feb. 13, 2024

(54) DRIVER ASSISTANCE SYSTEM

(71) Applicant: MAZDA MOTOR CORPORATION, Hiroshima (JP)

(72) Inventors: Yoshihiro Yamamoto, Hiroshima (JP); Yasuyuki Tonohara, Hiroshima (JP); Keiichi Yamasaki, Hiroshima (JP); Katsuhisa Maedo, Hiroshima (JP); Kenichi Nakamoto, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 118 days.

(21) Appl. No.: 17/614,037

(22) PCT Filed: Jun. 17, 2020

(86) PCT No.: PCT/JP2020/023821
§ 371 (c)(1),
(2) Date: Nov. 24, 2021

(87) PCT Pub. No.: WO2020/256025
PCT Pub. Date: Dec. 24, 2020

(65) Prior Publication Data
US 2022/0234644 A1 Jul. 28, 2022

(30) Foreign Application Priority Data
Jun. 18, 2019 (JP) .................. 2019-112728

(51) Int. Cl.
*B62D 1/04* (2006.01)
*B60K 26/02* (2006.01)
*B60K 26/04* (2006.01)

(52) U.S. Cl.
CPC .............. *B62D 1/046* (2013.01); *B60K 26/02* (2013.01); *B60K 26/04* (2013.01); *B60K 2026/046* (2013.01)

(58) Field of Classification Search
CPC .. B60K 26/02; B60K 26/04; B60K 2026/028; B60K 2026/046; B62D 1/04;
(Continued)

(56) References Cited

U.S. PATENT DOCUMENTS 872,478 A * 12/1907 Thum .................. B60K 26/02
477/206
1,593,876 A * 7/1926 Learmont .............. B60K 26/02
180/335
(Continued)

FOREIGN PATENT DOCUMENTS

| CN | 2792851 Y | 7/2006 |
| EP | 0 114 673 A1 | 8/1984 |

(Continued)

OTHER PUBLICATIONS

Machine Translation of FR-2911700-A1.*
(Continued)

*Primary Examiner* — Daniel D Yabut
(74) *Attorney, Agent, or Firm* — Studebaker & Brackett PC

(57) ABSTRACT

A driver assistance system is provided that allows a driver to easily perform an accelerator operation by a finger of his/her hand while grasping a steering holding section. The driver assistance system includes an operation member near a steering wheel held by a driver, which rotates about a rotation shaft in a vehicle front-rear direction and thereby steers the vehicle. The operation member has an operation section that the driver can manually operate to accelerate/decelerate the vehicle, and includes a support member on the steering wheel, the support member supporting the operation member in a slidingly displaceable manner along a steering axial direction. The operation section is disposed near a radially inner side of a rim section of the steering wheel, and the operation section and the rim section overlap in the
(Continued)

steering axial direction within a movable range of the operation member along the steering axial direction.

8 Claims, 12 Drawing Sheets

(58) Field of Classification Search
CPC .......... B62D 1/043; B62D 1/046; B62D 1/06; B62D 1/065; B62D 1/08; B62D 1/10
See application file for complete search history.

(56) References Cited

U.S. PATENT DOCUMENTS

| | | | | |
|---|---|---|---|---|
| 2,392,539 | A * | 1/1946 | Leible | B62D 1/065 219/204 |
| 3,226,997 | A * | 1/1966 | Malloy | B60K 26/02 74/532 |
| 5,947,227 | A | 9/1999 | Kempf | |
| 8,366,547 | B2 * | 2/2013 | Haswell | A63F 13/211 463/6 |
| 9,393,867 | B2 * | 7/2016 | Downey | G05G 1/04 |
| 2004/0143379 | A1 * | 7/2004 | Borroni-Bird | B60T 7/085 701/36 |
| 2018/0111671 | A1 * | 4/2018 | Shibayama | G05D 1/0206 |
| 2018/0251203 | A1 * | 9/2018 | Shibayama | B62D 1/046 |

FOREIGN PATENT DOCUMENTS

| | | | | |
|---|---|---|---|---|
| EP | 0 634 301 A1 | | 1/1995 | |
| EP | 0 647 540 A1 | | 4/1995 | |
| EP | 0829388 A2 | * | 3/1998 | ............ B60K 26/02 |
| FR | 2911700 A1 | * | 7/2008 | ............ B60K 26/02 |
| FR | 2917342 A1 | * | 12/2008 | ............ B60K 26/02 |
| JP | H10-181378 A | | 7/1998 | |
| WO | WO-2007051523 A1 | * | 5/2007 | ............ B60K 20/06 |
| WO | 2010/046941 A1 | | 4/2010 | |
| WO | WO-2010109510 A1 | * | 9/2010 | ............ B06K 26/02 |

OTHER PUBLICATIONS

Machine Translation of FR-2917342-A1.*
International Search Report issued in PCT/JP2020/023821; dated Aug. 25, 2020.
The extended European search report issued by the European Patent Office dated Jun. 15, 2023, which corresponds to European Patent Application No. 20826366.5-1012 and is related to U.S. Appl. No. 17/614,037.

* cited by examiner

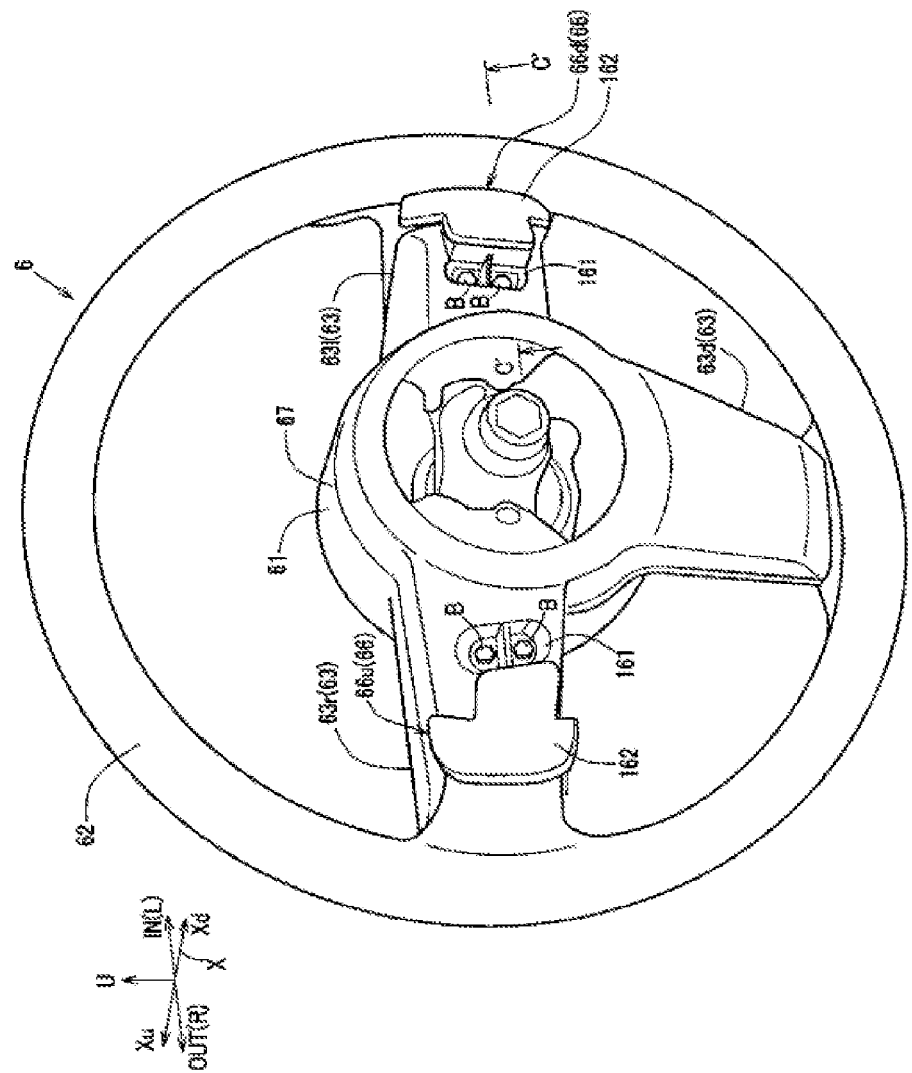

DRIVER ASSISTANCE SYSTEM

TECHNICAL FIELD

The present disclosure relates to a driver assistance system for a physically impaired person, with which a driver having a lower limb disorder and seated on a driver's seat manually performs an accelerator operation (an accelerating/decelerating operation) of a vehicle, and in detail, to a driver assistance system including an operation section, with which the driver manually performs the accelerator operation of the vehicle, in the vicinity of a steering holding section such as a steering wheel held by the driver to steer the vehicle.

BACKGROUND ART

As exemplified in each of European Patent No. 0634301 and International Publication WO 2010/046941, in order to enable a physically impaired person with a lower limb disorder (a lower limb impaired person), who has difficulty in performing depression operations of a brake pedal and an accelerator pedal by foot, to perform an accelerator operation of a vehicle by a manual operation while steering a steering holding section in a seated state on a driver's seat, a driver assistance system that is provided with an operation section for the accelerator operation of the vehicle near the steering holding section has been proposed.

In the driver assistance system disclosed in each of European Patent No. 0634301 and International Publication WO 2010/046941, an initial position of the operation section (a neutral position at which the driver does not operate the operation section) is set at a position separated from the steering holding section to the driver side. When the driver presses the operation section from the above initial position to a side near the steering holding section by a thumb or the like of his/her hand in a state of holding the steering holding section, the vehicle is accelerated according to a pressing amount thereof.

However, in the driver assistance system disclosed in each of European Patent No. 0634301 and International Publication WO 2010/046941, when being pressed to the side near the steering holding section, the operation section possibly interferes with the steering holding section, which restricts further pressing of the operation section.

In other words, in the case where a sufficient movement range (pressing stroke) of the operation section cannot be secured, a gradient of an acceleration characteristic, which represents a relationship between the pressing amount and acceleration of the vehicle, becomes steep. As a result, difficulty in the stable accelerator operation for the vehicle is a concern.

Meanwhile, in order to secure the movement range of the operation section, the initial position of the operation section has to be set at a position further separated from the steering holding section to the driver side. Such a case is disadvantageous for a pressing operation of the operation section by a finger, such as the thumb, of the hand when holding the steering holding section. As a result, degraded operability of the operation section is a problem.

SUMMARY

The present disclosure has been made in view of such problems and therefore has a purpose of providing a driver assistance system that allows a driver to easily perform an accelerator operation by a finger while grasping a steering holding section.

The present disclosure relates to a driver assistance system for a vehicle having a steering holding section that is held by a driver who is seated on a driver's seat, rotates about a rotation shaft in a vehicle front-rear direction, and thereby steers a vehicle. The driver assistance system includes an operation member near the steering holding section, the operation member having an operation section disposed such that the driver can manually operate the operation section to accelerate/decelerate the vehicle, includes a support member on the steering holding section, the support member supporting the operation member in a slidingly displaceable manner along a rotational axial direction in which the rotation shaft extends, and includes transmission means that mechanically or electrically transmits a sliding displacement amount in the rotation shaft direction of the operation member to an output control section of a drive source for the vehicle. When the steering holding section is seen from the driver side, the operation section is disposed along the steering holding section at a position near the rotation shaft side of the steering holding section. A movable range of the operation member is set such that, in the rotation shaft direction, the operation section is displaced at least from an end surface on the driver side of the steering holding section or from the driver side of the end surface to an overlapping area with the steering holding section.

With the above configuration, the driver can easily perform an accelerator operation by a finger of his/her hand while grasping the steering holding section.

In an aspect of the present disclosure, a spoke that couples the steering holding section and the rotation shaft is provided therebetween when seen from the driver side, and the support member is fixed to a rear back side of the spoke when seen from the driver side.

With the above configuration, the operation member can be fixed to the spoke with favorable appearance when seen from the driver side by fixing the support section to the rear back side (a back side) of the spoke when seen from the driver side.

In an aspect of the present disclosure, the operation section is disposed such that the operation section is divided by a portion corresponding to the spoke when the steering holding section is seen from the driver side. The operation member includes: the operation section; and a coupling section that couples one side and another side of the divided operation sections. The coupling section is disposed to extend across the corresponding spoke from the rear back side thereof when seen from the driver side.

With the above configuration, the operation member including the portions corresponding to the spoke sections when seen from the driver side can continuously be formed along the steering wheel.

In this way, of the plural operation sections that are disposed to be divided by the portions corresponding to the spoke sections in a circumferential direction of the steering wheel, even when the driver operates (presses) any of the operation sections, an operation amount (a pressing amount) thereof can be equalized among the operation sections.

In addition, since the coupling section is arranged to bypass the spoke section from the rear back side thereof when seen from the driver side, it is possible to secure the appearance when seen from the driver side by providing the operation member near the steering wheel, and it is possible to avoid interference of the coupling section with the corresponding spoke section when the operation member is pressed to the steering wheel side.

In an aspect of the present disclosure, the operation member is at least supported at three points by the steering holding section via the support member, and these at least three points of support sections are separately provided to the spokes on both of right and left sides of the rotation shaft when seen from the driver side.

With the above configuration, the operation member is at least supported at the three points, and these at least three points of the support sections are separately provided to the spokes on the right and left sides. As a result, while the plural operation sections, which are disposed to be mutually divided, are integrally formed via the coupling sections in the driver side view, the operation member can smoothly and slidingly be displaced along the rotation shaft direction without rattling or straying, which is caused by a tilt with respect to the steering holding section during an operation of the operation member.

In an aspect of the present disclosure, the spoke is provided with a cored bar that constitutes a framework of the spoke, the cored bar is provided with an attachment hole used to fixedly attach an auxiliary machine that can be operated manually while the steering holding section is held, and together with the auxiliary machine, the support member is attached to the cored bar by using the attachment hole.

With the above configuration, it is possible to improve assemblability to a base vehicle by also using the attachment hole, which is used to fixedly attach the auxiliary machine and is originally provided in the cored bar of the spoke, as the attachment hole used to fixedly attach the support member.

In an aspect of the present disclosure, the transmission means has a sensor that detects a displacement amount of the operation section, and the sensor is arranged in an area on the rotation shaft side from the steering holding section and on a lower side of the spoke extending in a vehicle width direction when seen from the driver side.

With the above configuration, it is possible to secure visibility of a display section, such as a meter, that is located in front of the driver's seat without being blocked by the sensor.

According to the present disclosure, the driver can easily perform the accelerator operation by the finger of his/her hand while grasping the steering holding section.

BRIEF DESCRIPTION OF THE DRAWINGS

FIG. 12 is a perspective view in which a steering wheel in a base vehicle before modification is seen from the opposite driver side and the right side.

DETAILED DESCRIPTION

A vehicle in this embodiment is created by modifying a right-hand drive vehicle of a mass production type as a base vehicle (an existing vehicle), for example, and, due to the modification of the existing vehicle, includes a driver assistance system that assists with a manual accelerator operation such that a lower limb impaired person who has difficulty in performing a depression operation of an accelerator pedal by foot can perform the accelerator operation by a manual operation while steering a steering wheel in a seated state on a driver's seat.

Figure 1:
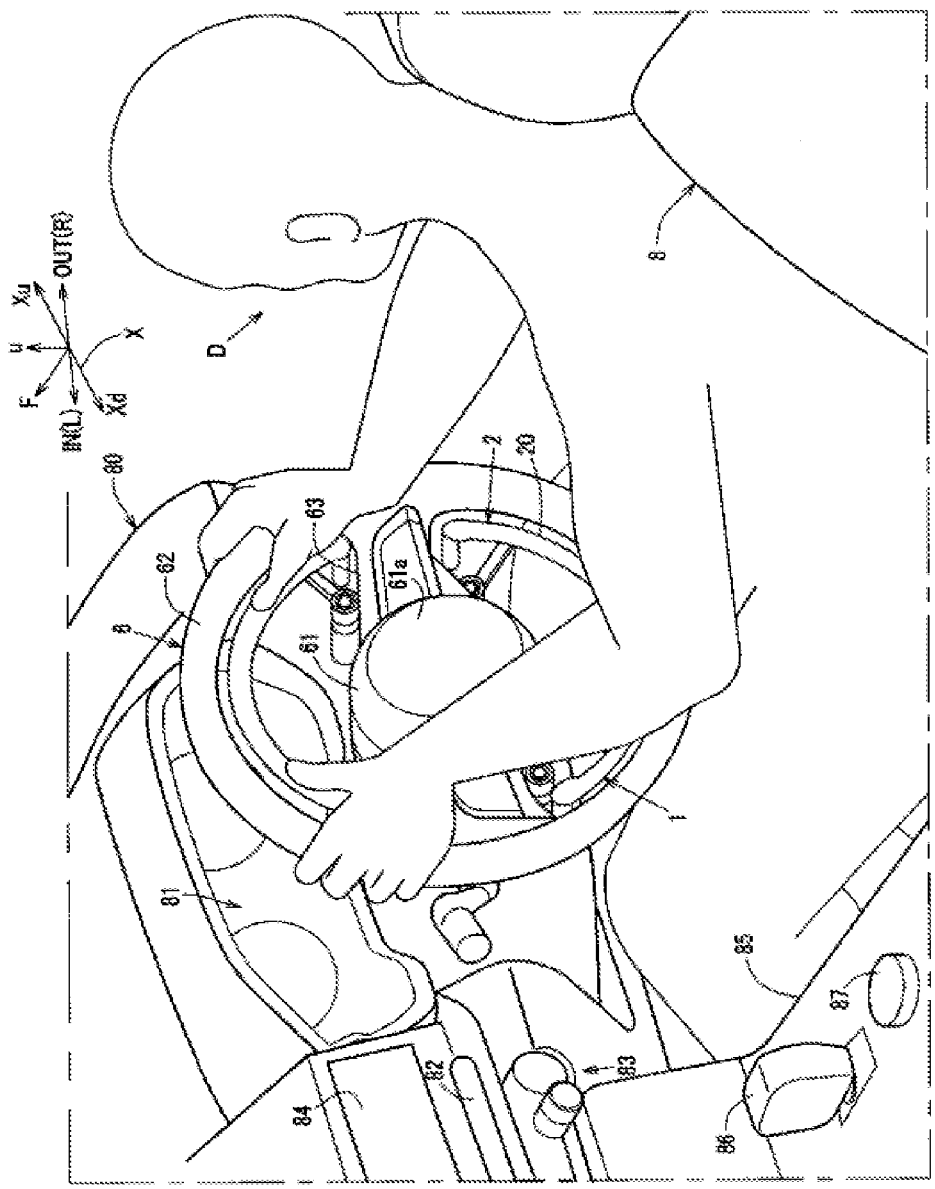
FIG. 1 is an external appearance view illustrating a situation where a vehicle including a driver assistance system in this embodiment is driven.
Figure 2:
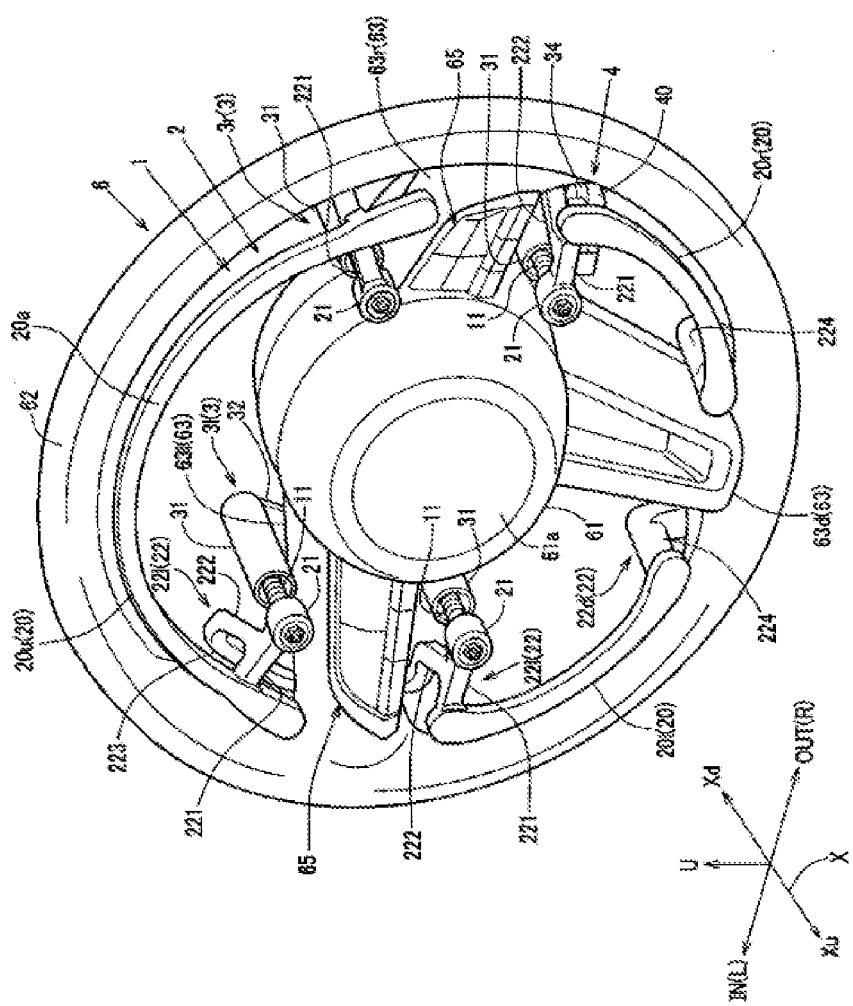
FIG. 2 is a perspective view in which a steering wheel provided with an operation member in the embodiment is seen from a driver side and a right side.
Figure 3:
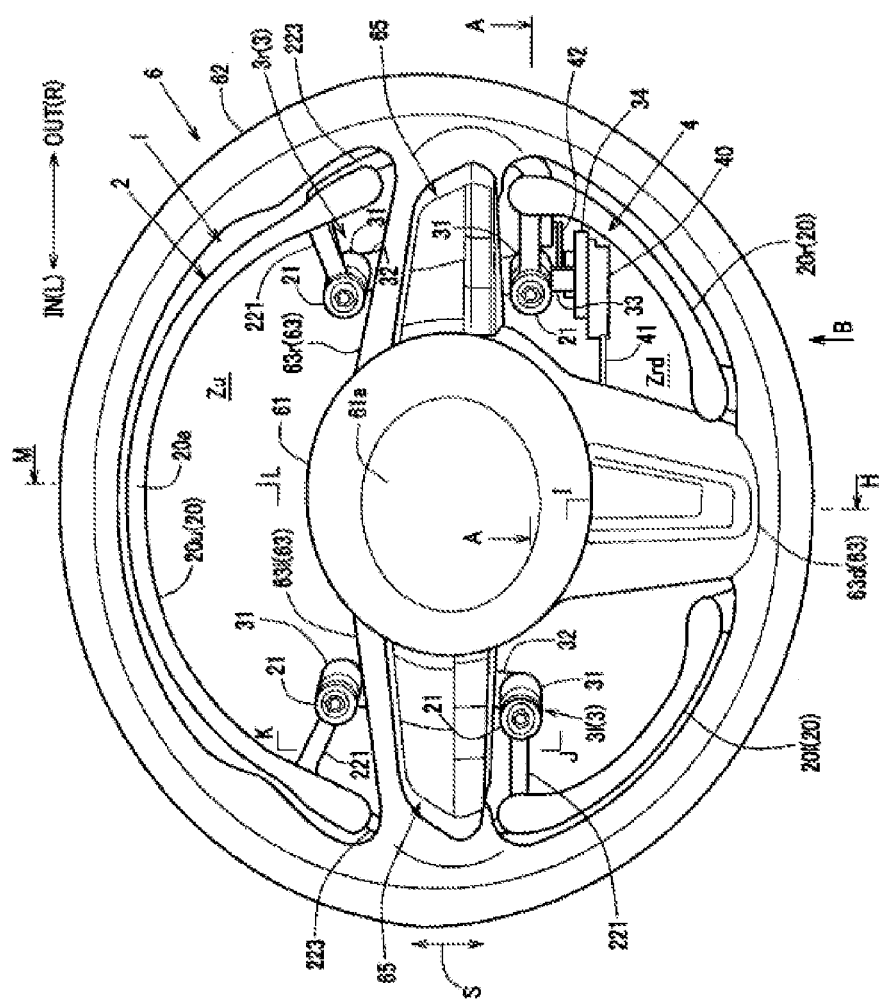
FIG. 3 is a front view in which the steering wheel provided with the operation member in the embodiment is seen from the driver side.
Figure 4:
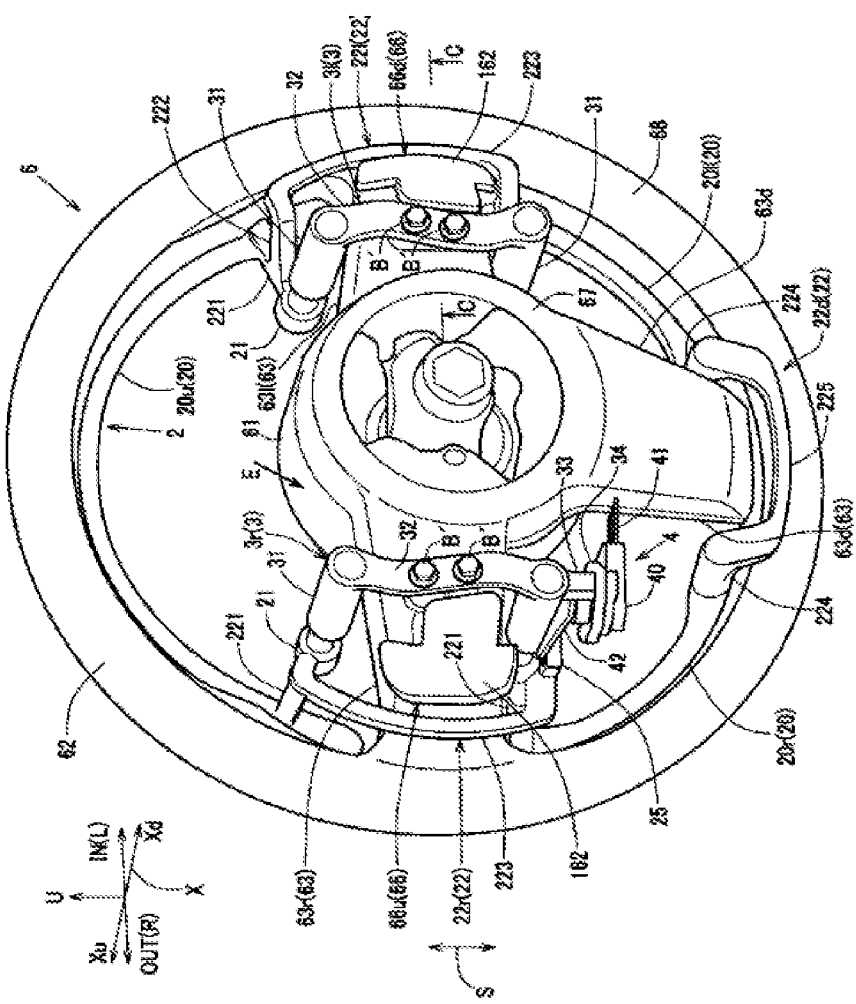
FIG. 4 is a perspective view in which the steering wheel provided with the operation member in the embodiment is seen from an opposite driver side and the right side.
Figure 5:
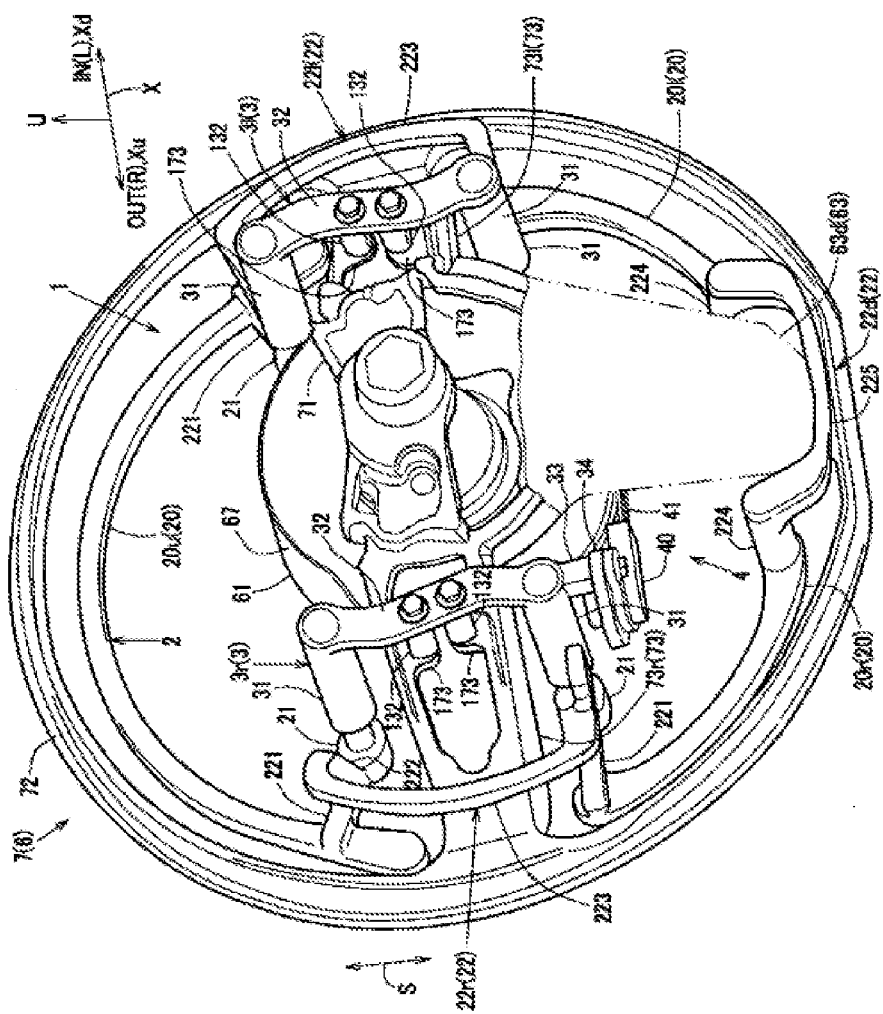
FIG. 5 is a perspective view in which the steering wheel provided with the operation member in the embodiment and illustrated only by a cored bar in its entirety is seen from the opposite driver side and the right side.
Figure 6A:
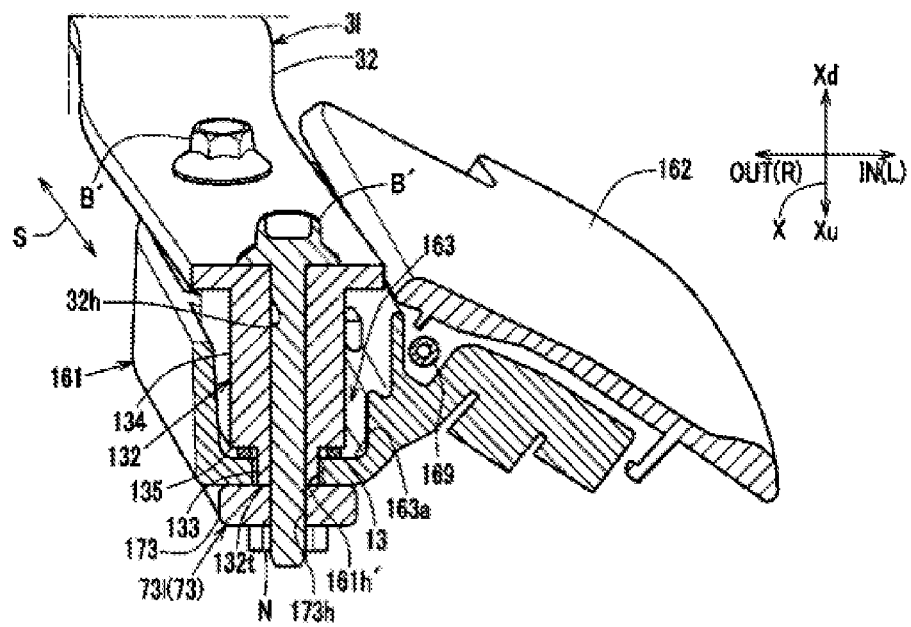
FIG. 6A is a cross-sectional perspective view illustrating a main section that is taken along line C-C in FIG. 4.
Figure 6B:
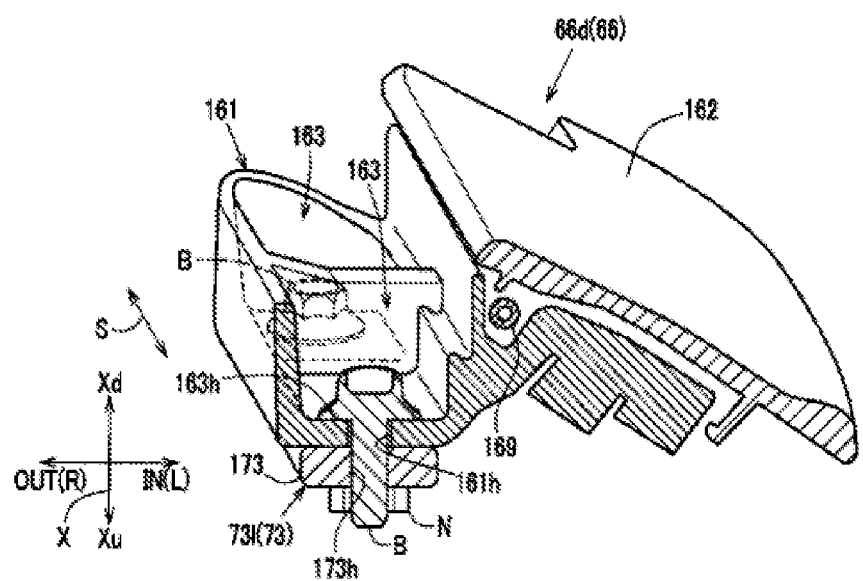
FIG. 6B is a perspective view illustrating a main section that is taken along line C'-C' in FIG. 12.
Figure 7:
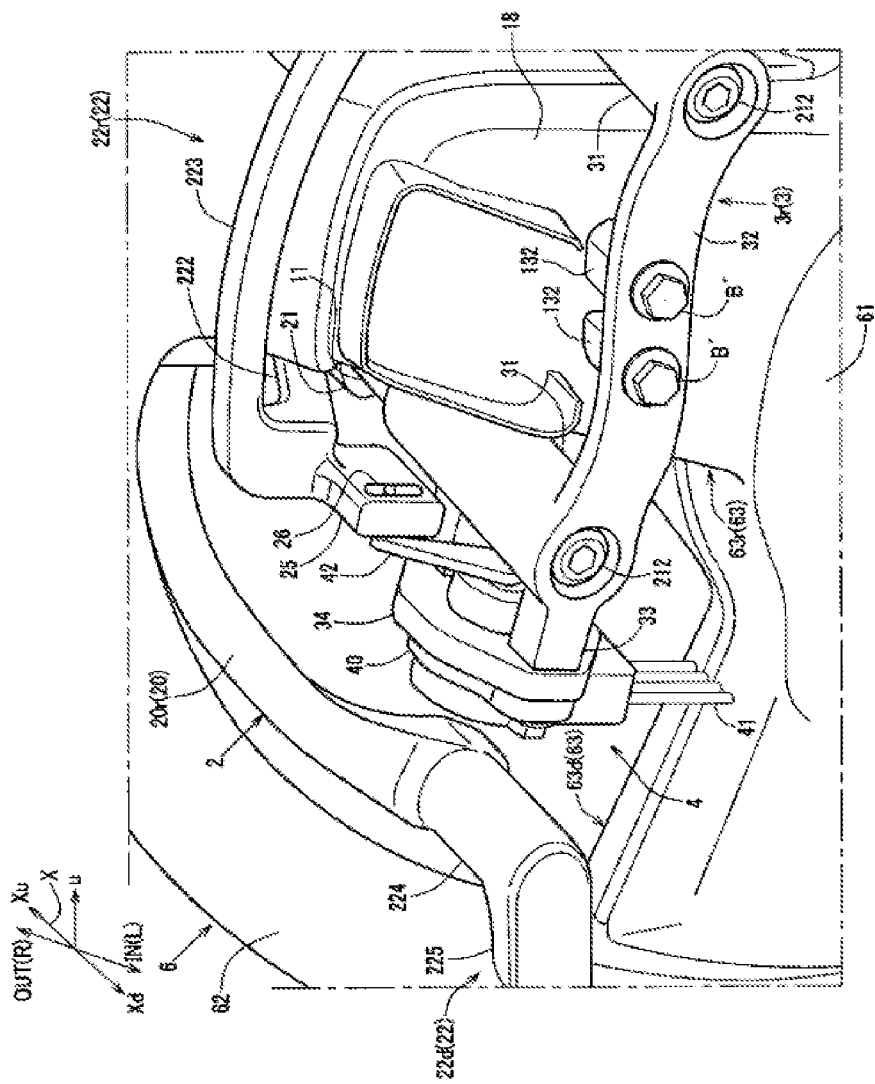
FIG. 7 is an enlarged view that is seen from an arrow E in FIG. 4 and illustrates a main section while omitting a paddle shifter.
Figure 8:
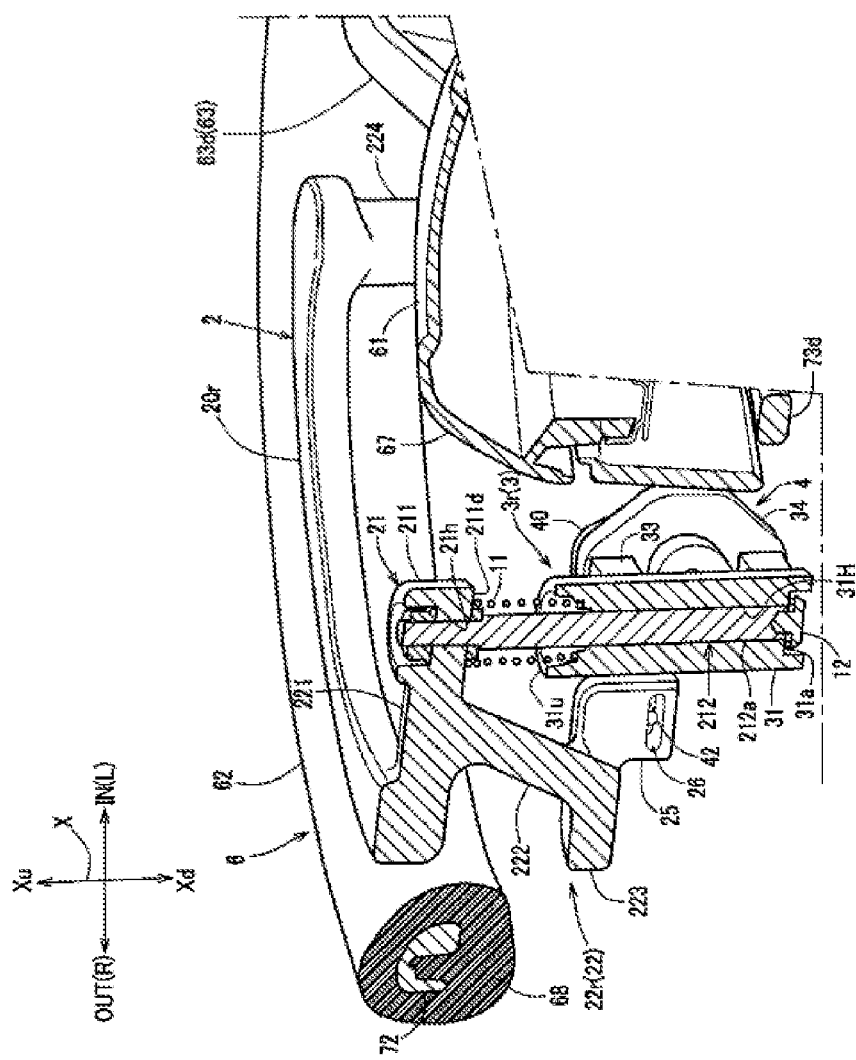
FIG. 8 is a cross-sectional perspective view illustrating a main section that is taken along line A-A in FIG. 3.
Figure 9:
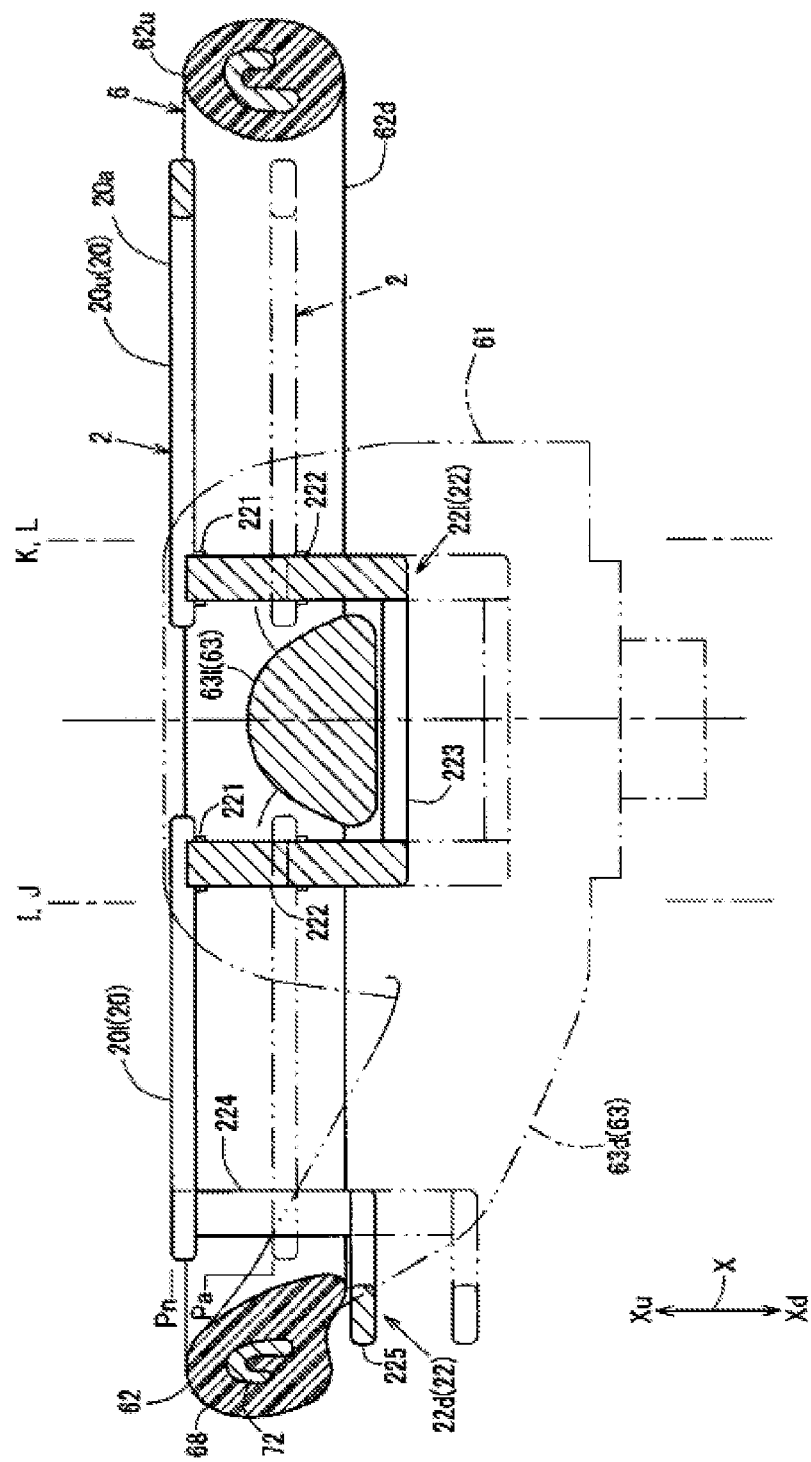
FIG. 9 is an explanatory view of a movable range of the operation member that schematically illustrates a rim section and the operation member in a cross section.
Figure 10:
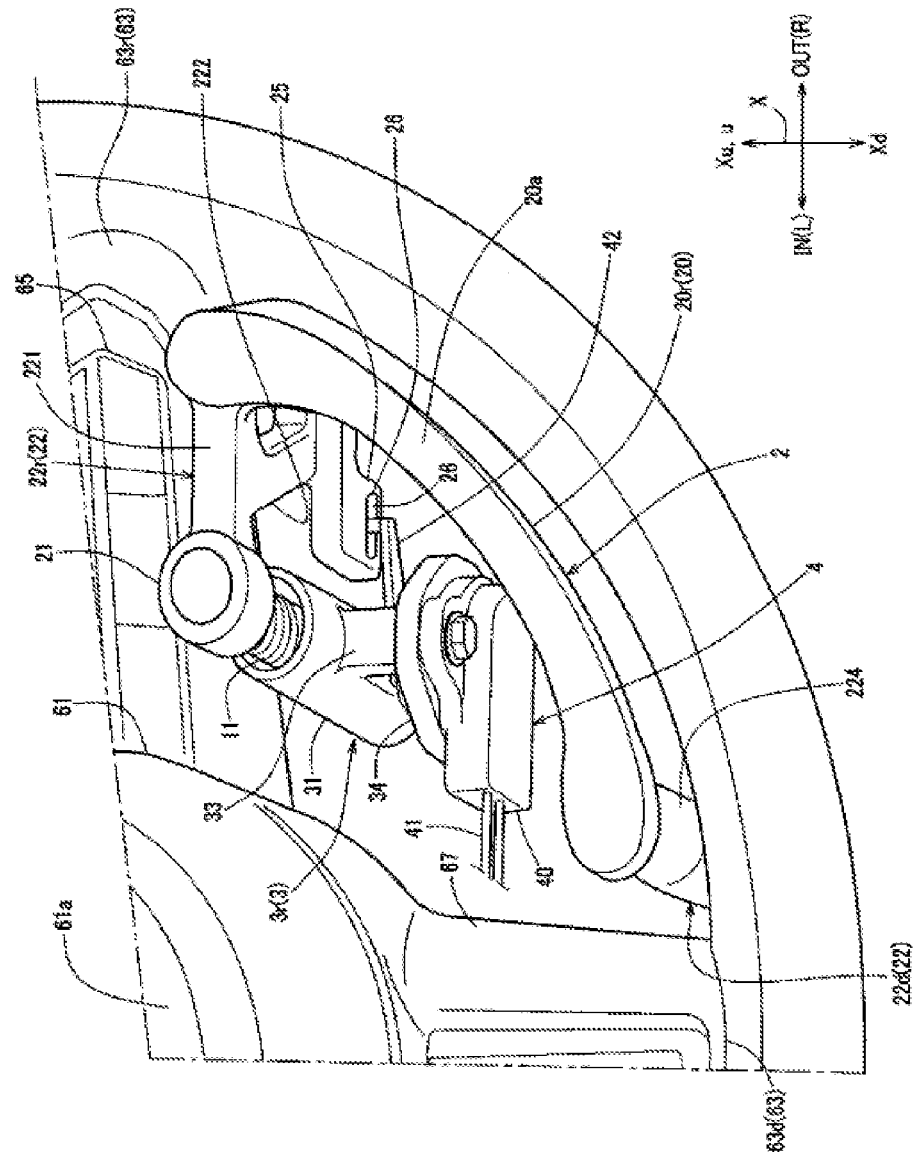
FIG. 10 is an enlarged view of a main section that is seen from an arrow B in FIG. 3.

A detailed description will hereinafter be made on an embodiment of the present disclosure with reference to the drawings. FIG. 1 is an external appearance view illustrating a main structure around a driver's seat of a vehicle, in which the driver assistance system of this embodiment is incorporated, and a situation where a driver drives the vehicle, FIG. 2 is a perspective view in which a steering wheel provided with an operation member in the embodiment is seen from the driver side and a right side, FIG. 3 is a front view in which the steering wheel provided with the operation member in the embodiment is seen from the driver side, FIG. 4 is a perspective view in which the steering wheel provided with the operation member in the embodiment is seen from an opposite driver side and the right side, and FIG. 5 is a perspective view in which the steering wheel provided with the operation member in the embodiment and illustrated only by a cored bar in its entirety is seen from the opposite driver side and the right side. FIG. 6A is a cross-sectional perspective view illustrating a main section that is taken along line C-C in FIG. 4 and is a cross-sectional perspective view illustrating a main section of an attachment structure of a support member to a spoke section cored bar, and FIG. 6B is a perspective view illustrating a main section that is taken along line C'-C' in FIG. 12 and is a cross-sectional perspective view illustrating a main section of an attachment structure of a paddle shifter to the spoke section cored bar before modification of the base vehicle. FIG. 7 is an enlarged view that is seen from an arrow E in FIG. 4 and illustrates a main section while omitting the paddle shifter, FIG. 8 is a cross-sectional perspective view illustrating a main section that is taken along line A-A in FIG. 3, FIG. 9 is an explanatory view of a movable range of the operation member and schematically illustrates a rim section and the operation member in a cross section that is taken along lines H-I-J-K-L-M in FIG. 3, FIG. 10 is an enlarged view of a main section that is seen from an arrow B in FIG. 3, and FIG. 12 is a perspective view in which the steering wheel in the base vehicle before the modification is seen from the opposite driver side and the right side.

In the drawings, an arrow F indicates a vehicle front direction, an arrow U indicates a vehicle up direction, an arrow OUT indicates an outer side in a vehicle width direction, an arrow IN indicates an inner side in the vehicle width direction, an arrow R indicates a vehicle right side, an arrow L indicates a vehicle left side, X indicates an axial direction of the steering wheel, Xu indicates an upper side (the driver side) in the axial direction of the steering wheel, and Xd indicates a lower side (an opposite side from the driver side) in the axial direction of the steering wheel.

As illustrated in FIG. 1, a driver's seat 8 and a passenger's seat (not illustrated) are respectively mounted on right and left sides in a front portion of a cabin floor in the vehicle. A steering wheel 6 that is operated in a state of being held by a driver D who is seated on the driver's seat 8 is provided in front of the driver's seat 8.

At a front end of the cabin, an instrument panel 80 is provided across the entire cabin in the vehicle width direction. A center console 85 is attached between the driver's seat 8 and the passenger's seat in the front portion of the cabin floor, and a front portion thereof is integrally connected to a central portion in the vehicle width direction of the instrument panel 80. The center console 85 constitutes a part of an interior member of the cabin and has a shift knob 86, a start switch 87, and the like disposed at such positions that the driver D who is seated on the driver's seat 8 can operate those by his/her left hand.

In the instrument panel 80 in front of the driver's seat 8, a display section 81 including various instruments such as a tachometer and a speedometer is disposed in a visually recognizable manner over the steering wheel 6. In a portion on the left side thereof and above the connected portion with the front portion of the center console 85, an air conditioning outlet 82 and various operation buttons 83, such as setting dials for an audio system and an air conditioner, are disposed. Furthermore, in a portion above these, a display 84 of a navigation system is provided.

On the floor in front of the driver's seat 8 in the cabin, an accelerator pedal (not illustrated) is provided at a position at which the driver D seated on the driver's seat 8 places his/her right foot. A brake pedal (not illustrated) is provided at a position near and on a left side of the accelerator pedal (on a central side in the vehicle width direction). Both the accelerator pedal and the brake pedal are normal pedals provided in the base vehicle.

In addition, as illustrated in FIG. 2 and FIG. 3, the above-described steering wheel 6 includes: a base section 61 that is coupled to a steering shaft, which is not illustrated; a rim section 62 that is held by the driver D and arranged in a ring shape with the base section 61 being a center on an outer circumferential side of the base section 61 when seen from the driver D side (hereinafter described as "in the driver D side view") in an axial direction of the steering shaft (hereinafter abbreviated as a "steering axial direction"); and plural spoke sections 63, each of which extends radially from the base section 61 to the rim section 62.

In this example, the three spoke sections 63 are provided and include: a right spoke section 63r that extends rightward from the base section 61 in the driver D side view in the steering axial direction (that is, in front view); a left spoke section 63l that extends leftward; and a lower spoke section 63d that extends downward.

As illustrated in FIG. 2 and FIG. 3, a horn 61a is provided on the driver D side in the steering axial direction of the base section 61, and is pressed to produce horn sound (warning sound).

Operation switches 65 are disposed on the driver D side in the steering axial direction of each of the right and left spoke sections 63, and are used to operate in-vehicle equipment such as the audio system and the navigation system.

In addition, as illustrated in FIG. 4, the steering wheel 6 includes paddle shifters 66 that respectively correspond to upshifting and downshifting.

In this example, an upshifting paddle shifter 66u is provided to the right spoke section 63r, and a downshifting paddle shifter 66d is provided to the left spoke section 63l.

As illustrated in FIG. 5, the steering wheel 6 has a cored bar 7 as a frame member, and the cored bar 7 has: a base section cored bar 71 that corresponds to the base section 61; a ring-shaped rim section cored bar 72 that corresponds to the rim section 62; and spoke section cored bars 73 (a right spoke section cored bar 73r, a left spoke section cored bar 73l, and a lower spoke section cored bar 73d (see FIG. 8)), each of which corresponds to respective one of the spoke sections 63. The base section cored bar 71 and the spoke section cored bars 73 are each covered with a cover 67 that is made of resin, and the rim section cored bar 72 is covered with urethane 68 or the like. In FIG. 5, a detailed structure of the base section cored bar 71 is not illustrated, only a ridgeline representing an outer shape of the lower spoke section 63d is illustrated by an imaginary line, and an internal structure thereof is not illustrated.

As illustrated in FIG. 4 and FIG. 6A, the above-described paddle shifters 66u, 66d each include a paddle shifter base section 161 and a lever 162, both of which are made of the resin.

The paddle shifter base section 161 is fixedly fastened to the spoke section cored bar 73 by bolts B' and the like from a rear back surface side of the paddle shifter base section 161, that is, an opposite side from the driver D side (hereinafter described as an "opposite driver D side") in the steering axial direction.

As illustrated in FIG. 6A, one end of the lever 162 is swingably and pivotally supported by the paddle shifter base section 161 via a shaft 169 that extends vertically cross the spoke section cored bar 73 from a rear back side in the steering axial direction of the spoke section cored bar 73.

In this way, the paddle shifters 66 are configured to allow the driver D to manually upshift/downshift such that a gear stage is increased one-by-one every time the driver D operates the lever 162, which is provided in the upshifting paddle shifter 66u, during travel of the vehicle and that the gear stage is lowered one-by-one every time the driver D operates the lever 162, which is provided in the downshifting paddle shifter 66d, during the travel of the vehicle.

Next, a description will be made of a driver assistance system 1 (a manual accelerating/decelerating operation assistance system) in this embodiment that is incorporated in the above-described base vehicle. As illustrated in FIG. 1 to FIG. 5, the driver assistance system 1 includes: an operation member 2 that performs an accelerating/decelerating operation of the vehicle when being slidingly displaced along the steering axial direction; a support member 3 that supports the operation member 2 to be slidable along the steering axial direction; and transmission means 4 that detects a sliding displacement amount of the operation member 2 and transmits, as a signal, the detected sliding displacement amount to an ECU that controls an opening degree of a throttle valve of an engine.

The operation member 2 is disposed near the steering wheel 6, and is integrally formed by including: plural operation sections 20, each of which is operated, for example, when being pressed downward (to the opposite driver D side) in the steering axial direction by a thumb or the like of the driver D's hand that holds the steering wheel 6; a slide supported section 21 that is supported by the support member 3 in a slidable manner along the steering axial direction; and a coupling section 22 that couples the plural operation sections 20 and couples the operation section 20 and the slide supported section 21.

As illustrated in FIG. 2 and FIG. 3, in the driver D side view in the steering axial direction, the operation section 20 is disposed near an inner side of the rim section 62 of the steering wheel 6, in other words, near a radially inner side of the rim section 62 (near a side having the base section 61). In the operation section 20, an upper surface 20a in the steering axial direction is formed to be flat so as to be easily pressed by a ball of the thumb of the driver D's hand that holds the steering wheel 6.

Furthermore, as illustrated in FIG. 2 and FIG. 3, in the driver D side view in the steering axial direction, the operation sections 20 are disposed to be divided by portions corresponding to the spoke sections 63 and are each formed in an arcuate shape along the rim section 62.

In detail, the three operation sections 20 include: an upper operation section 20u that are disposed above both of the left and right spoke sections 63l, 63r in the driver D side view in the steering axial direction; a lower right operation section 20r that is disposed between the right spoke section 63r and the lower spoke section 63d; and a lower left operation section 20l that is disposed between the left spoke section 63l and the lower spoke section 63d.

As illustrated in the same drawings, in the driver D side view in the steering axial direction, the slide supported section 21 is disposed on each of upper and lower sides (each side of an arrow S in FIG. 3) of the right spoke section 63r and each of upper and lower sides (each of the sides of the arrow S in FIG. 3) of the left spoke section 63l. Two each of the slide supported sections 21 are provided to right and left sides of the operation member 2 in a manner to correspond to respective support sections 31, which will be described below, in the support member 3. Here, the arrow S in FIG. 3 indicates a disposed direction of the steering wheel 6 in vehicle side view, that is, an up-down direction of the steering wheel 6.

As illustrated in FIG. 4 and FIG. 5, the coupling section 22 includes: a right coupling section 22r that couples the upper operation section 20u and the lower right operation section 20r; a left coupling section 22l that couples the upper operation section 20u and the lower left operation section 20l; and a lower coupling section 22d that couples the lower right operation section 20r and the lower left operation section 20l. The right coupling section 22r is disposed in a portion corresponding to the right spoke section 63r, the left coupling section 22l is disposed in a portion corresponding to the left spoke section 63l, and the lower coupling section 22d is disposed in a portion corresponding to the lower spoke section 63d.

Since the right coupling section 22r and the left coupling section 22l have bilaterally-symmetrical shapes, a description will herein be made of structures of these coupling sections 22 on the basis of a configuration of the right coupling section 22r. As illustrated in FIG. 2, FIG. 4, FIG. 5, and FIG. 8 to FIG. 10, the right coupling section 22r is integrally formed by including: a radial coupling side 221 on each of upper and lower sides that extends in the radial direction of the steering wheel 6 (the rim section 62) at a position near respective one of the upper and lower sides of the right spoke section 63r; an axial coupling side 222 that extends substantially downward in the steering axial direction from an intermediate portion of the radial coupling side 221 on each of the upper and lower sides; and a circumferential coupling side 223 (see FIG. 4 and FIG. 5) that couples these axial coupling sides 222 on the upper and lower sides in a circumferential direction of the steering wheel 6.

Of the radial coupling sides 221 on the upper and lower sides, the upper radial coupling side 221 has a radially outer end that is connected to a front portion at a lower right end in an extending direction of the upper operation section 20u, and has a radially inner end that is coupled to the slide supported section 21 near and on the upper side of the right spoke section 63r.

Of the radial coupling sides 221 on the upper and lower sides, the lower radial coupling side 221 has a radially outer end that is coupled to a front portion at an upper right end in an extending direction of the lower right operation section 20r, and has a radially inner end that is coupled to the slide supported section 21 on the lower side of the right spoke section 63r.

As illustrated in FIG. 4, the circumferential coupling side 223 extends arcuately in a manner to cross (extend across) the right spoke section 63r from the rear back side (the opposite driver D side) in the steering axial direction, and couples lower ends in the steering axial direction of the axial coupling sides 222, 222 on the upper and lower sides.

Next, a description will be made of a configuration of the lower coupling section 22d. As illustrated in FIG. 4 and FIG. 5, the lower coupling section 22d is integrally formed by including: an axial coupling side 224 on a left side that is located near a left side of the lower spoke section 63d and extends substantially downward in the steering axial direction from a front portion at a lower right end in an extending direction of the lower left operation section 20l; an axial coupling side 224 on a right side that is located near a right side of the lower spoke section 63d and extends substantially downward in the steering axial direction from a front portion at a lower left end in an extending direction of the lower right operation section 20r; and a circumferential coupling side 225 that couples these axial coupling sides 224, 224 on the left and right sides in the circumferential direction of the steering wheel 6.

As illustrated in FIG. 4 and FIG. 5, the lower coupling section 22d is integrally formed by including: the axial coupling side 224 on the left side that is disposed near the left side of the lower spoke section 63d; the axial coupling side 224 on the right side that is disposed near the right side of the lower spoke section 63d; and the circumferential coupling side 225 that couples these axial coupling sides 224, 224 on the left and right sides in the circumferential direction of the steering wheel 6.

Both of the axial coupling side 224 on the left side and the axial coupling side 224 on the right side extend substantially downward in the steering axial direction from the front portion at the lower right end in the extending direction of the lower left operation section 20l and the front portion at the lower left end in the extending direction of the lower right operation section 20r, respectively.

The circumferential coupling side 225 in the lower coupling section 22d extends arcuately in a manner to cross (extend across) from the rear back side (the opposite driver D side) in the steering axial direction, and couples lower end portions in the steering axial direction of the axial coupling sides 224, 224 on the left and right sides.

Here, the lower coupling section 22d does not include the radial coupling side 221, and the support member 3 is not attached to the lower spoke section 63d. That is, the operation member 2 is not fixedly attached to the lower spoke section 63d of the steering wheel 6.

As described above, the operation member 2 is integrally formed by coupling the three operation sections 20 (20u, 20r, and 20l), which are disposed to be divided by the portions corresponding to the spoke sections 63 in the driver D side view in the steering axial direction, by the coupling sections 22 in a manner to bypass the corresponding spoke sections 63 from the rear back side.

Next, a description will be made of the support member 3. As illustrated in FIG. 4, the support member 3 is provided to correspond to each of the right spoke section 63r and the left spoke section 63l, and these support members 3 (a right support member 3r and a left support member 3l) on the right and left sides are formed in bilaterally-symmetrical shapes except for portions, which will particularly be described.

The support members 3 on the left and right sides are fixedly attached to the corresponding left and right spoke sections 63l, 63r, respectively and, as described above, support the operation member 2 in the slidable manner along the steering axial direction.

The support member 3 is integrally formed by including: the support section 31 that supports the slide supported section 21 of the operation member 2 in the slidable manner along the steering axial direction as illustrated in FIG. 2 to FIG. 5, FIG. 7, and FIG. 8; and an attachment section 32 that is fixedly attached to the rear back surface side (the opposite driver D side) of the spoke section 63 in the steering axial direction as illustrated in FIG. 4, FIG. 5, and FIG. 7.

The support section 31 in the support member 3 and the slide supported section 21 in the operation member 2 constitute a support structure for the operation member 2 by the support member 3. A description will hereinafter be made of the support structure.

As illustrated in FIG. 3, the support section 31 is disposed on and near each of upper and lower sides (both sides of the arrow S in FIG. 3) of respective ones of the left and right spoke sections 63l, 63r and, as illustrated in FIG. 8, is formed in a cylindrical shape having a through hole 31H that is formed to penetrate the support section 31 along the steering axial direction, that is, in a bush shape.

As illustrated in FIG. 8, an upper end portion 211 in the steering axial direction of the slide supported section 21 is coupled to the radially inner end of the radial coupling side 221 in the radial direction of the steering wheel 6 as described above. The upper end portion 211 of the slide supported section 21 is formed with a through hole 21h that penetrates the upper end portion 211 along the steering axial direction. The slide supported section 21 includes a shaft 212 constructed of a bolt that is fastened to the upper end portion 211 in a state of being inserted through the through hole 21h of the upper end portion 211 in a manner to be projected downward in the steering axial direction from the upper end portion 211 of the slide supported section 21.

In this shaft 212, an outer circumferential surface of a projected portion 212a from the upper end portion 211 of the slide supported section 21 is formed smoothly. By inserting the projected portion 212a through the through hole 31H of the support section 31, the shaft 212 slides in the steering axial direction in a state of being guided by an inner circumferential surface of the through hole 31H.

In this way, as illustrated in FIG. 2 to FIG. 5, in the driver D side view in the steering axial direction, the support members 3, which are attached to each of the left and right spoke sections 63, support the operation member 2 at two positions near the upper and lower sides (both of the sides of the arrow S in FIG. 3) of respective one of the left and right spoke sections 63. In other words, the entire operation member 2 is supported at a total of four positions (four-point support), which are two each of the left and right positions, by the steering wheel 6 via the support members 3 on the left and right sides.

Furthermore, as illustrated in FIG. 8, the support structure includes a coil-shaped urging spring 11 that is disposed to surround the shaft 212 of the slide supported section 21 from an outer side along a direction of the shaft 212. In the steering axial direction, the urging spring 11 in a compressed state is interposed between the upper end portion 211 of the slide supported section 21 and the support section 31 and urges the slide supported section 21 in the up direction (toward the driver D side) from the support section 31.

At a lower end of the shaft 212 (the bolt) provided to the slide supported section 21, an upward movement stopper 12 that is engaged with a circumferential edge 31a of the through hole 31H on a lower surface of the support section 31 is provided.

At an upper limit position (a maximum upward movement position) in a movable range of the operation member 2, which slides along the steering axial direction, that is, a position at which the operation member 2 comes the closest to the driver D side, the upward movement stopper 12 is engaged with the circumferential edge 31a of the through hole 31H on the lower surface of the support section 31.

In this way, with the urging spring 11, the upward movement stopper 12 restricts further upward movement of the operation member 2, which is urged upward in the steering axial direction, from the upper limit position (that is, removal of the shaft 212 from the through hole 31H).

In addition, since being urged upward by the urging spring 11, the operation member 2 is always located at the upper limit position in the movable range of the operation member 2 in a state of not being pressed by the driver D. That is, the upper limit position corresponds to a neutral position Pn at which the accelerating operation, which will be described below, is not performed on the operation member 2.

As illustrated in FIG. 9, as a position at which the thumb or the like of the driver D's hand holding the steering wheel 6 can press the upper surface 20a (a pressing surface) of the operation section 20 downward in the steering axial direction, the neutral position Pn of the operation member 2 is set to be located on the slightly upper side (the slightly driver D side) of an upper end surface 62u of the rim section 62 of the steering wheel 6 in the steering axial direction.

In this example, in the steering axial direction, the upper surface 20a of the operation section 20 is set to be located approximately 5 mm to 20 mm (preferably approximately 5 mm to 15 mm, further preferably approximately 10 mm) above the upper end surface 62u of the rim section 62 of the steering wheel 6. With such a setting, it is possible to reduce a muscle load from an initial position of the operation section 20 to a fully pressed state and to minimize a fluctuation in the muscle load.

When the thumb or the like of the driver D's hand that holds the steering wheel 6 presses the operation section 20 of the operation member 2 downward (the opposite driver D side) in the steering axial direction from the neutral position Pn against an urging force of the urging spring 11, the driver assistance system 1 can perform the accelerating operation of the vehicle. Meanwhile, when the thumb or the like is released from the operation section 20 in the pressed state, the operation member 2 gradually returns to the neutral position Pn due to the urging force of the urging spring 11, and the driver assistance system 1 can thereby perform the decelerating operation.

Here, the movable range of the operation member 2 that is slidingly displaced along the steering axial direction includes a range where the upper surface 20a of the operation section 20 of the operation member 2 overlaps the rim section 62 of the steering wheel 6 in the steering axial direction.

However, the operation member 2 is slidingly displaced such that, regardless of a pressing amount from the neutral position Pn, the operation section 20 of the operation member 2 is disposed on the inner side of the rim section 62 (the radially inner side of the rib) in the driver D side view in the steering axial direction and that, as the operation section 20 is pressed from the neutral position Pn, the coupling section 22 separates downward from the spoke section 63.

In this way, the operation member 2 does not interfere with the steering wheel 6 in the steering axial direction despite the overlap with the steering wheel 6, and can be pressed downward (to the steering wheel 6 side) in the steering axial direction from the neutral position Pn.

In addition, as illustrated in FIG. 8, the operation member 2 can slide downward in the steering axial direction until a lower surface 211d of the upper end portion 211 in the slide supported section 21 abuts an upper end 31u of the support section 31.

A position at which the lower surface 211d of the upper end portion 211 in the slide supported section 21 abuts the upper end 31u of the support section 31 is a position at which the operation member 2 is farthest from the driver D in the movable range of the operation member 2, and corresponds to a maximum acceleration position Pa (a maximum pressing position) of the operation member 2 as illustrated in FIG. 8.

In this example, as illustrated in FIG. 8, the maximum acceleration position Pa is set to a position at which at least a part of the operation member 2, which is pressed to the maximum acceleration position Pa, overlaps the steering wheel 6 in the steering axial direction. However, the maximum acceleration position Pa is not limited thereto. The maximum acceleration position Pa may be set such that the entire operation member 2 is located below the steering wheel 6 in the steering axial direction. That is, it may be set that, at the maximum acceleration position Pa, the upper surface 20a of the operation section 20 in the operation member 2 is pressed to be located below a lower end surface 62d of the rim section 62 in the steering wheel 6 in the steering axial direction.

Next, a description will be made of an attachment structure of the attachment section 32 to each of the spoke sections 63l, 63r including a structure of the attachment section 32 of the support member 3. In this embodiment, when the driver assistance system 1 is assembled to the base vehicle, an attachment structure of the paddle shifter 66, which is originally provided to the spoke section 63 of the steering wheel 6, to the spoke section cored bar 73 (see FIG. 6B) as illustrated in FIG. 12 in the base vehicle before the modification is used. Then, as illustrated in FIG. 6A, the attachment section 32 of the support member 3 is fixedly fastened to the spoke section cored bar 73 by the bolts B' and the like. Thus, prior to the description of the attachment structure of the attachment section 32 to the spoke section 63 in this embodiment, a brief description will be made of the attachment structure of the paddle shifter 66 to the spoke section 63 in the base vehicle.

As illustrated in FIG. 12, in each of the spoke sections 63l, 63r on the left and right sides of the steering wheel 6 in the base vehicle before the modification, the spoke section cored bar 73 (see FIG. 5) is formed with a paddle shifter attachment flange 173 (see FIG. 5 and FIG. 6B), to which the paddle shifter base section 161, which is provided in the paddle shifter 66 and is made of the resin, as illustrated in FIG. 6B and FIG. 12 is fixedly fastened from the rear back surface side (the opposite side from the driver D) in the steering axial direction by a bolt B and the like.

In the opposite driver D side view in the steering axial direction, a pair of the paddle shifter attachment flanges 173 are provided on upper and lower sides (both of the sides of the arrow S in FIG. 5) of the spoke section cored bar 73 (see FIG. 5), and is each formed with a through hole 173h that penetrates the paddle shifter attachment flange 173 in the steering axial direction as illustrated in FIG. 6B. Meanwhile, a through hole 161h is formed in a portion of the paddle shifter base section 161 that corresponds to the through hole 173h formed in the spoke section cored bar 73. On a rear back surface (a surface on an opposite side of a surface on a side that is attached to the spoke section cored bar 73) in the steering axial direction of the paddle shifter base section 161, a counterbore section 163 in which a circumferential edge of the through hole 161h is formed to be recessed from a peripheral portion in the opposite driver D side view.

Then, as illustrated in FIG. 6B, the bolt B is inserted through the through hole 161h of the paddle shifter base section 161 and the through hole 173h of the paddle shifter attachment flange 173 in this order from the rear back surface side in the steering axial direction. In this way, the paddle shifter base section 161 is fixedly fastened to the paddle shifter attachment flange 173 that is formed on each of the upper and lower sides of the spoke section cored bar 73.

In this embodiment, as illustrated in FIG. 6A, based on the attachment structure of the paddle shifter 66 to the spoke section cored bars 73 in such a base vehicle, the support member 3 is attached to each of the left and right spoke section cored bars 73. More specifically, additional processing is performed on the paddle shifter base section 161 illustrated in FIG. 6A to increase a diameter of the through hole 161h.

As a result, as illustrated in FIG. 6A, a through hole 161h' formed in the paddle shifter base section 161 is formed to have a slightly larger inner diameter than the through hole 173h formed in the paddle shifter attachment flange 173 of the spoke section cored bar 73.

By the way, as illustrated in FIG. 4 and FIG. 7, the attachment section 32 provided to the support member 3 in this embodiment extends in the up-down direction (to each of the sides in the S direction in FIG. 4) in a manner to cross the corresponding spoke section 63 in the opposite driver D side view in the steering axial direction, and is coupled to the support section 31 that is provided near each of the upper and lower sides of the spoke section 63.

As illustrated in FIG. 4, FIG. 7, and FIG. 6A, a projected piece 132 that is projected in the up direction of the steering axial direction, that is, to the paddle shifter base section 161 side is integrally formed in an intermediate portion in an extending direction of the attachment section 32, that is, a portion corresponding to the through hole 161h' on each of the upper and lower sides of the paddle shifter base section 161 in the opposite driver D side view in the steering axial direction.

As illustrated in FIG. 6A, the projected piece 132 on each of the upper and lower sides is formed in a stepped shape by having: a tip section 133 in a projected direction thereof; and a base section 134 formed to have a larger diameter than the tip section 133 and by having a step section 135 between these tip section 133 and base section 134.

The base section 134 of the projected piece 132 can be inserted through the counterbore section 163 of the paddle shifter base section 161, and is formed to have a larger outer diameter than the inner diameter of the through hole 161h' in the paddle shifter base section 161. The tip section 133 of the projected piece 132 can be inserted through the through hole 161h' of the paddle shifter base section 161, and is formed to have a larger outer diameter than the inner diameter of the through hole 173h formed in the paddle shifter attachment flange 173.

Furthermore, a through hole 32h is formed in a portion of the attachment section 32 corresponding to the projected piece 132 in the opposite driver D side view of the steering axis, and penetrates the attachment section 32 along the steering axial direction, that is, a center axis of the projected piece 132.

As illustrated in FIG. 6A, in a state where the base section 134 of the projected piece 132 is inserted through the counterbore section 163 of the paddle shifter base section 161 and the tip section 133 is inserted through the through hole 161h', the bolt B', which is longer than the bolt B (see FIG. 6B) used to fasten the paddle shifter base section 161 to the spoke section cored bar 73 in the above-described base vehicle, is inserted through the through hole 32h of the attachment section 32 and the through hole 173h of the spoke section cored bar 73 in this order from the rear back surface side in the steering axial direction.

In this state, an end surface 132t of the tip section 133 in the projected piece 132 comes into pressure-contact with a circumferential edge of the through hole 173h on the rear back surface of the paddle shifter attachment flange 173, and the step section 135, which is formed on the outer circumferential surface of the projected piece 132, comes into pressure-contact with a bottom surface 163a of the counterbore section 163 in the paddle shifter base section 161 via an O-ring 13 and the like. In this way, together with the paddle shifter base section 161, the support section 31 is fixedly fastened to the spoke section cored bar 73 by using the bolts B' and nuts N.

As illustrated in FIG. 3 to FIG. 5, FIG. 7, and FIG. 10, the above-described transmission means 4 includes: a sensor 40 that detects the sliding displacement amount of the operation member 2; an electrical wiring 41 that transmits, as the signal, the sliding displacement amount detected by the sensor 40 to the ECU that controls the opening degree of the throttle valve of the engine; and the like.

Here, as described above, the three operation sections 20, which are disposed in the circumferential direction of the rim section 62, in the operation member 2 are integrally formed via the coupling sections 22. Thus, in this example, as illustrated in FIG. 2 to FIG. 5, the only one sensor 40, which detects the sliding displacement amount of the operation member 2, is provided, that is, near the lower side of the right spoke section 63r in the driver D side view in the steering axial direction.

More specifically, as illustrated in FIG. 3 to FIG. 5, FIG. 7, FIG. 8, and FIG. 10, in the support section 31, which is disposed near the lower side of the right spoke section 63r (an area Zrd in FIG. 3), in the right support member 3r in the driver D side view in the steering axial direction, a support arm 33 extends downward from a lower portion in the steering axial direction of the support section 31. A sensor attachment section 34 is integrally formed at a lower end (a tip in an extending direction) of the support arm 33, and the sensor 40 is attached to the sensor attachment section 34 and is thereby supported by the right support member 3r.

The sensor 40 includes a swing lever 42, a tip of which swings in a manner to approach or separate from the operation member 2 in the steering axial direction, and is configured to be able to detect a swing angle of the swing lever 42.

Meanwhile, as illustrated in FIG. 7, FIG. 8, and FIG. 10, the right coupling section 22r in the operation member 2 is integrally formed with a swing lever engagement section 25 that extends downward in the steering axial direction from a coupled portion with the circumferential coupling side 223 and the axial coupling side 222 and is engaged with the tip of the swing lever 42.

As illustrated in FIG. 7, FIG. 8, and FIG. 10, the swing lever engagement section 25 is formed with an elongated engagement hole 26. When the tip section 133 of the swing lever 42 is engaged with a circumferential edge of this engagement hole 26, the tip section of the swing lever 42 swings in response to the sliding displacement in the steering axial direction of the operation member 2. As a result, the sensor 40 can detect the sliding displacement amount of the operation member 2.

As illustrated in FIG. 1, the driver assistance system 1 in this above-described embodiment is the driver assistance system for the vehicle having the steering wheel 6 (the steering holding section) that is held by the driver D who is seated on the driver's seat 8 and steers the vehicle when rotating about the steering shaft (the rotation shaft) in the vehicle front-rear direction. As illustrated in FIG. 4, FIG. 5, FIG. 7, and FIG. 8, the driver assistance system 1 includes the operation member 2, which has the operation sections 20 disposed such that the driver D can manually accelerate/decelerate the vehicle, near the rim section 62 of the steering wheel 6, includes the support members 3, each of which supports the operation member 2 in the slidingly displaceable manner along the steering axial direction X (the rotational axial direction) in which the steering shaft (not illustrated) extends, on the steering wheel 6, and, as illustrated in FIG. 2 to FIG. 4, FIG. 7, FIG. 8, and FIG. 10, includes the transmission means 4 that mechanically or electrically transmits the sliding displacement amount in the steering axial direction of the operation member 2 to the ECU (the output control section) that controls the opening degree of the throttle valve of the engine (the drive source) in the vehicle. As illustrated in FIG. 2 to FIG. 5, in the driver D side view of the steering wheel 6, the operation sections 20 are disposed on the steering shaft side of the rim section 62 of the steering wheel 6, that is, near the base section 61 side (the radially inner side of the rim section 62) along the rim section 62 of the steering wheel 6. As illustrated in FIG. 9, the movable range of the operation member 2 is set such that, in the steering axial direction, the operation section 20 is displaced at least from the position above the upper side (the driver D side) of the upper end surface 62u of the rim section 62 (the end surface on the driver D side of the steering wheel 6) to the overlapping area with the steering wheel 6 (rim section 62).

As described above, the operation section 20 is disposed along the rim section 62 near the side having the base section 61 from the rim section 62 in the driver D side view of the steering wheel 6 (see FIG. 3). Thus, as illustrated in FIG. 1, while holding the steering wheel 6, the driver D presses the operation section 20 downward in the steering axial direction (to the steering wheel 6 side) by the thumb or the like of his/her hand holding the steering wheel 6, and can thereby manually perform the accelerator operation.

Furthermore, at the time, the operation section 20 can move to the overlapping area with the steering wheel 6 in the steering axial direction as described above (see FIG. 9). Thus, even when the driver D presses the operation section 20, the operation member 2 does not interfere with the spoke section 63 of the steering wheel 6, and the like.

For this reason, when pressing the operation section 20 by the thumb or the like of the hand holding the steering wheel 6, the driver D can firmly press the operation section 20 by using a large muscle in a bulged portion of a base of the thumb (the ball of the thumb). Therefore, the driver D can easily perform the accelerator operation.

In addition, unlike the conventional operation member, a pressing stroke of the operation member 2 in this embodiment can be secured along the steering axial direction of the operation section 20 without setting a position that is significantly separated upward (to the driver D side) from the upper end surface 62*u* of the rim section 62 as the upper limit position (the neutral position) in the movable range of the operation section in consideration of the interference of the operation member with the spoke section 63 of the steering wheel 6 and the like when the operation section is pressed.

As an aspect of the present disclosure, as illustrated in FIG. 4, FIG. 5, and FIG. 7, the spoke section 63 (the spoke) that couples the rim section 62 and the base section 61 (the steering shaft) of the steering wheel 6 is provided therebetween, and the support member 3 is fixed to the rear back side of the spoke section 63 in the driver D side view in the steering axial direction.

With the above configuration, the operation member 2 can be fixedly attached to the spoke section 63 via the support member 3 with favorable appearance in the driver D side view by fixedly attaching the support section 31 to the spoke section 63 from the rear back side thereof in the steering axial direction.

Furthermore, by fixedly attaching the support section 31 to the spoke section 63 from the rear back side thereof in the steering axial direction, the support member 3 can easily be attached to the spoke section 63 while avoiding the movable range of the operation member 2, which is slidingly displaced to the overlapping area with the steering wheel 6 (the rim section 62) in the steering axial direction. As a result, such a layout can be adopted that the operation member 2 can easily avoid the interference with the support member 3 including the attachment portion of the support member 3 to the spoke section 63 when the operation member 2 is pressed.

In an aspect of the present disclosure, as illustrated in FIG. 2 and FIG. 3, the operation sections 20 are disposed such that the operation sections 20 are divided by the portions corresponding to the spoke sections 63 in the driver D side view (in the circumferential direction of the steering wheel 6). As illustrated in FIG. 4, FIG. 5, FIG. 7, and FIG. 9, the operation member 2 includes: the operation sections 20; and the coupling sections 22, each of which couples the one side and the other side of the portions, which correspond to the respective spoke section 63, in the divided operation sections 20. In the driver D side view, each of the coupling sections 22 is disposed to extend across the corresponding spoke section 63 from the rear back side thereof.

With the above configuration, the operation member 2 including the portions corresponding to the spoke sections 63 in the driver D side view can continuously be formed along the steering wheel 6.

In this way, of the plural operation sections 20 that are disposed to be divided by the portions corresponding to the spoke sections 63 in the circumferential direction of the steering wheel 6, even when any of the operation sections 20 is operated, an operation amount (the pressing amount) thereof can be equalized among the operation sections 20. Thus, even in the case where the different operation section 20 is pressed to slide while the steering wheel 6 is rotating (steering), the vehicle can stably be accelerated or decelerated.

In addition, since the coupling section 22 of the operation member 2 is arranged to bypass the spoke section 63 from the rear back side thereof in the driver D side view, it is possible to secure the appearance in the driver D side view by providing the operation member 2 near the steering wheel 6, and it is possible to avoid the interference of the coupling section 22 with the corresponding spoke section 63 when the operation member 2 is pressed to the steering wheel 6 side.

In an aspect of the present disclosure, as illustrated in FIG. 2 to FIG. 5, the operation member 2 is at least supported at three points by the steering wheel 6 via the support member 3, that is, the four points in this example. These at least three points of the support sections 31 are separately provided to the right spoke section 63*r* and the left spoke section 63*l*, that is, two points each in this example.

With the above configuration, the operation member 2 is at least supported at the three points, and these at least three points of the support sections 31 are separately provided to the left and right spoke sections 63*l*, 63*r*. As a result, while the plural operation sections 20, which are disposed to be mutually divided, are integrally formed via the coupling sections 22 in the driver D side view, the operation member 2 can smoothly and slidingly be displaced along the steering axial direction without rattling or straying, which is caused by a tilt in the steering axial direction during the operation of the operation member 2.

In an aspect of the present disclosure, as illustrated in FIG. 5, the right spoke section 63*r* is provided with the right spoke section cored bar 73*r* (the cored bar) that constitutes a framework of the right spoke section 63*r*, and the left spoke section 63*l* is provided with the left spoke section cored bar 73*l* (the cored bar) that constitutes a framework of the left spoke section 63*l*. Each of these spoke section cored bars 73*l*, 73*r* on the left and right sides is provided with the paddle shifter attachment flange 173 (see FIG. 5). The paddle shifter attachment flange 173 is provided with the through hole 173*h* (the attachment hole) (see FIG. 6A) used to fixedly attach the paddle shifter base section 161 of the paddle shifter 66 (the auxiliary machine) that can be operated manually while the steering wheel 6 is held. Together with the paddle shifter 66, the support member 3 is attached to each of the left and right corresponding spoke section cored bars 73*l*, 73*r* by using the through hole 173*h*.

As described above, it is possible to improve assemblability to the base vehicle by also using the through hole 173*h*, which is used to fixedly attach the paddle shifter 66 and is originally provided in each of the spoke section cored bars 73*l*, 73*r* on the left and right sides, as the attachment hole used to fixedly attach the support member 3.

In an aspect of the present disclosure, as illustrated in FIG. 2 to FIG. 5, the transmission means 44 has the sensor 40 that detects the sliding displacement amount of the operation section 20. The sensor 40 is only arranged on the steering shaft (the rotation shaft) side from the rim section 62 of the steering wheel 6 in the driver D side view, that is, on the base section 61 side and in the area (see the area Zrd in FIG. 3) on the lower side in the up-down direction (see the arrow S in FIG. 3) of the steering wheel from the right and left spoke sections 63r, 63l (the right spoke section 63r in this example) extending in the vehicle width direction.

Just as described, the sensor 40 is arranged in the area on the base section 61 side (the radially inner side) from the rim section 62 and on the lower side of the right spoke section 63r in the driver D side view. In this way, a field of view of the driver D in the seated state on the driver's seat 8 is blocked by the sensor 40 as little as possible at the time when the driver D visually recognizes an area in front of the vehicle over the steering wheel 6 in the driver D side view, and his/her field of view can be secured.

More specifically, visibility of the area in front of the vehicle, which can visually be recognized by the driver D over an area (see an area Zu in FIG. 3) on the inner side of the rim section 62 and on the upper side of the right and left spoke sections 63r, 63l in the driver D side view, is not blocked by the sensor 40 unlike a case where the sensor 40 is arranged in the area Zu. Thus, for example, visibility of the display section 81 and the like, which is disposed in front of the driver's seat 8, can be secured.

The present disclosure is not limited to the configuration in the above-described embodiment, but can be implemented in various embodiments. For example, the driver assistance system 1 in this above-described embodiment relates to the manual acceleration/deceleration operation assistance system that allows the driver D to manually perform the accelerator operation. However, in a modified example of the above-described embodiment, the driver assistance system in the present disclosure may further include manual brake operation assistance means that allows the driver D to manually perform the brake operation.

Figure 11:
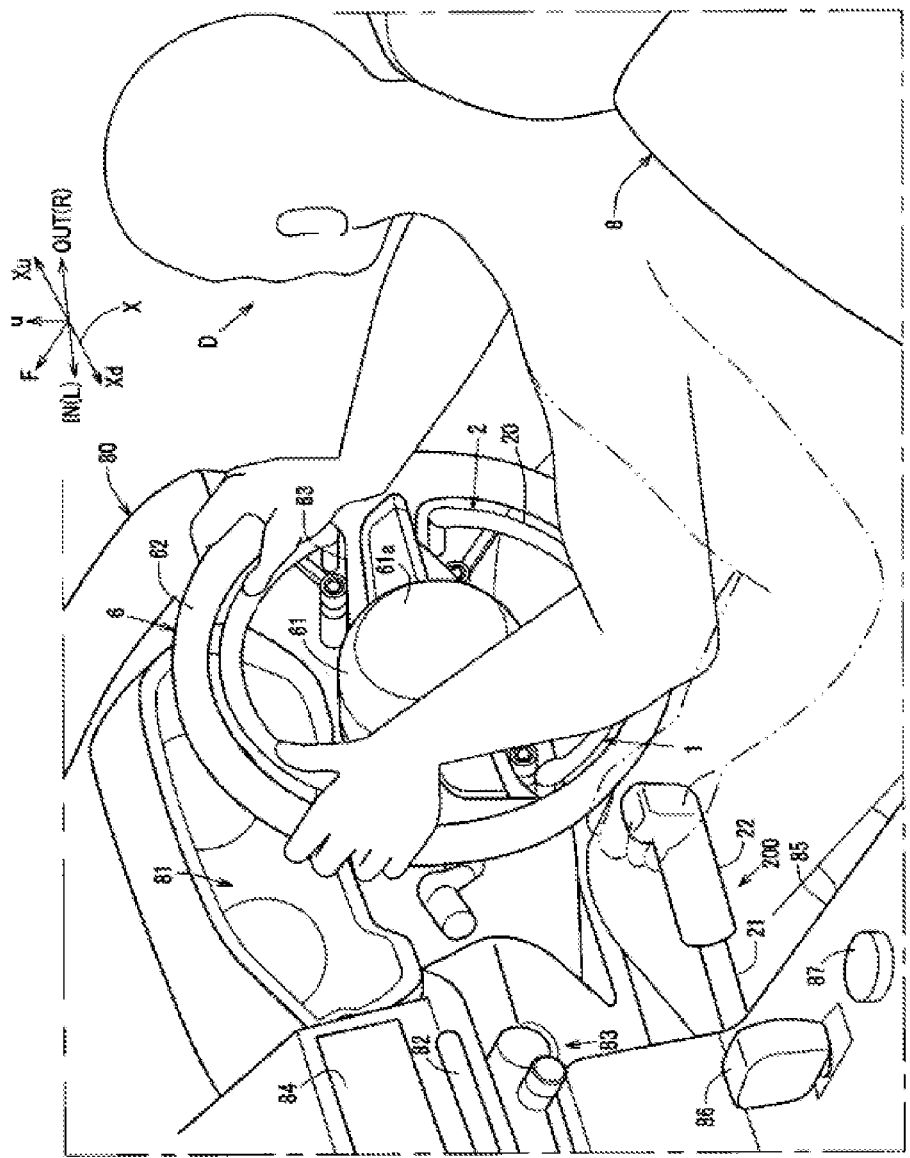
FIG. 11 is an external appearance view illustrating a situation where a vehicle including a driver assistance system in a modified example of the present disclosure is driven.

More specifically, as illustrated in FIG. 11, the manual brake operation assistance means is attached to an area where the driver D seated on a driver's seat 76 can manually operate the manual brake operation assistance means, for example, on a left side (the center console 85 side) of a steering wheel 70 near the driver's seat 76 in a vehicle body while keeping a tilted posture in which the manual brake operation assistance means is tilted downward from a rear portion to a front portion. The manual brake operation assistance means includes: an operation bar 200 that is manually operated by the driver D; a brake actuation section (not illustrated) that actuates a brake mechanism by slidingly displacing the operation bar 200 in a down front direction with the manual operation by the driver D; an accelerator actuation section (not illustrated) that actuates an accelerator mechanism by slidingly displacing the operation bar 200 in an up rear direction with the manual operation by the driver D.

In this way, as illustrated in FIG. 11, the driver D can also perform the brake operation manually in addition to the accelerator operation.

In regard to the accelerator operation, the manual operation may be performed when the driver D uses either the operation member 2, which is provided near the steering wheel 6, or the operation bar 200. However, the operation member 2 is advantageous since the driver D can perform the accelerator operation while holding the steering wheel 6.

For this reason, the manual brake operation assistance means may be configured not to include the above-described accelerator actuation section and the like, and may be configured such that only the brake operation can be performed by using the operation bar 200 that is slidable only in the down front direction.

In addition, in another embodiment, the setting of the upper end position (that is, the neutral position Pn) in the movable range of the operation member 2, which slides along the steering axial direction, is not limited to the position at which the upper surface 20a of the operation section 20 is located near the upper side (the driver D side) of the upper end surface 62u of the rim section 62 in the steering axial direction as described above, and the upper end position may be set to a position that matches the upper end surface 62u of the rim section 62.

What is claimed is:

1. A driver assistance system for a vehicle having a steering holding section that is held by a driver who is seated on a driver's seat, rotates about a rotation shaft in a vehicle front-rear direction, and thereby steers a vehicle, the driver assistance system comprising:

an operation member having an operation section disposed such that the driver can manually operate the operation section to accelerate/decelerate the vehicle when the steering holding section is held by the driver; and a support member that supports the operation member in a slidingly displaceable manner along a rotation shaft direction in which the rotation shaft extends; and transmission means that mechanically or electrically transmits a sliding displacement amount in the rotation shaft direction of the operation member to an output control section of a drive source for the vehicle, wherein when the steering holding section is seen from the driver side, the operation section is disposed along said steering holding section at a position proximal said steering holding section and between the steering holding section and the rotation shaft, and a movable range of the operation member is such that, in the rotation shaft direction, the operation section is movable from a first position closest to the driver where the operation section is aligned with an end surface on the driver side of the steering holding section in a direction normal to the rotation shaft direction, to a second position farthest from the driver overlapping with the steering holding section.

2. The driver assistance system according to claim 1, wherein a spoke that couples the steering holding section and the rotation shaft is provided therebetween when seen from the driver side, and the support member is fixed to a rear back side of the spoke when seen from the driver side.

3. The driver assistance system according to claim 2, wherein the operation section is disposed such that said operation section is divided by a portion corresponding to the spoke when the steering holding section is seen from the driver side, the operation member includes:
 the operation section; and
 a coupling section that couples one side and another side of the divided operation sections, and the coupling section is disposed to extend across the corresponding spoke from the rear back side thereof when seen from the driver side.

4. The driver assistance system according to claim 3, wherein a second spoke that couples the steering holding section and the rotation shaft is provided therebetween when seen from the driver side, the operation member is at least supported at three points by the steering holding section via the support member, and these at least three points of support sections are separately provided to the spoke and the second spoke on both of right and left sides of the rotation shaft when seen from the driver side.

5. The driver assistance system according to claim 4, wherein the spoke is provided with a cored bar that constitutes a framework of said spoke, the cored bar is provided with an attachment hole used to fixedly attach an auxiliary machine that can be operated manually while the steering holding section is held, and together with the auxiliary machine, the support member is attached to the cored bar by using the attachment hole.

6. The driver assistance system according to claim 5, wherein the transmission means has a sensor that detects a displacement amount of the operation section, and the sensor is arranged in an area on the rotation shaft side from the steering holding section and on a lower side of the spoke extending in a vehicle width direction when seen from the driver side.

7. The driver assistance system according to claim 2, wherein the spoke is provided with a cored bar that constitutes a framework of said spoke, the cored bar is provided with an attachment hole used to fixedly attach an auxiliary machine that can be operated manually while the steering holding section is held, and together with the auxiliary machine, the support member is attached to the cored bar by using the attachment hole.

8. The driver assistance system according to claim 2, wherein the transmission means has a sensor that detects a displacement amount of the operation section, and the sensor is arranged in an area on the rotation shaft side from the steering holding section and on a lower side of the spoke extending in a vehicle width direction when seen from the driver side.

* * * * *